United States Patent
Fox

(10) Patent No.: US 6,800,295 B2
(45) Date of Patent: Oct. 5, 2004

(54) WATER SOLUBLE SHEET COMPOSITION

(75) Inventor: Priscilla S. Fox, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 28 days.

(21) Appl. No.: 10/267,235

(22) Filed: Oct. 9, 2002

(65) Prior Publication Data

US 2004/0071755 A1 Apr. 15, 2004

(51) Int. Cl.$^7$ .......................... A61K 9/70; A61F 13/00
(52) U.S. Cl. .................................. 424/443; 424/400
(58) Field of Search ................... 424/400, 443

(56) References Cited

U.S. PATENT DOCUMENTS

| | | |
|---|---|---|
| 4,126,142 A | 11/1978 | Saute |
| 4,383,986 A | 5/1983 | Dubash et al. |
| 4,544,693 A * | 10/1985 | Surgant ............ 524/375 |
| 5,023,339 A | 6/1991 | Kato et al. |
| 5,385,737 A | 1/1995 | Shigeno et al. |
| 5,670,469 A | 9/1997 | Dingus et al. |
| 5,827,529 A | 10/1998 | Ono et al. |
| 5,843,415 A | 12/1998 | Klar |
| 5,853,706 A | 12/1998 | Klar |
| 5,948,430 A | 9/1999 | Zerbe et al. |
| 5,955,057 A | 9/1999 | Maunder et al. |
| 5,962,388 A | 10/1999 | Sherry et al. |
| 6,001,788 A | 12/1999 | Jaworski et al. |
| 6,017,517 A | 1/2000 | Park |
| 6,020,301 A | 2/2000 | Davister et al. |
| 6,060,547 A | 5/2000 | Canter et al. |

* cited by examiner

*Primary Examiner*—Thurman K. Page
*Assistant Examiner*—Konata M. George
(74) *Attorney, Agent, or Firm*—Snell & Wilmer LLP

(57) ABSTRACT

The present invention is a composition in the form of a soluble sheet or film which has a variety of uses, particularly in the personal care field. Such sheets are preferably water soluble. An important component of these water soluble sheets is a "base composition," which includes a water soluble film forming polymer, a polyvinyl alcohol, and a humectant such as propylene glycol. Surfactant may be added to the liquid base composition so that, when the composition is dried into sheet form, the sheet will generate foam when exposed to water and have cleansing properties. Skin care ingredients may also be added to the base composition in addition to or in place of the surfactant. Volatile alcohols or hydrocarbons may also be incorporated into the liquid base composition to facilitate drying of the composition to form the flexible sheet product.

26 Claims, No Drawings

WATER SOLUBLE SHEET COMPOSITION

FIELD OF THE INVENTION

The present invention relates to a composition in the form of a soluble sheet which has a variety of uses, particularly in the personal care field.

BACKGROUND OF THE INVENTION

The prior art discloses various uses for soluble films. For instance, soluble films have been used to enclose materials. U.S. Pat. No. 5,385,737 to Shigeno, et al. and U.S. Pat. No. 4,544,693 to Surgant disclose soluble capsules into which various substances can be placed.

Soluble films have also been used for cosmetic purposes. For example, U.S. Pat. No. 6,060,547 to Canter et al. discloses a water-in-oil emulsion film used to form a makeup foundation. Another cosmetic application of water soluble films is found in U.S. Pat. No. 4,126,142 to Saute, which discloses a face mask which is applied to the skin, allowed to dry, and then removed.

U.S. Pat. No. 5,948,430 to Zerbe, et al., discloses a soluble film for oral administration. The film is used for the delivery of materials via the mucous membranes, particularly the buccal mucosa.

Although means for forming films for various applications are known in the art, there is a need for a water soluble film which will bind surfactant and other ingredients, and which, when exposed to water, will dissolve and provide personal cleansing such as can be obtained from, for example, hand soap or body wash. There is also a need for a water soluble film to which skin care ingredients may be added and which will release such skin ingredients upon exposure to sufficient moisture.

SUMMARY OF THE INVENTION

The present invention is a composition in the form of a soluble sheet or film which has a variety of uses, particularly in the personal care field. Such sheets are preferably water soluble, which aids in their use in the personal care field. The water soluble sheets of this invention will bind surfactant and other ingredients, and which, when exposed to water, will dissolve and provide personal cleansing such as can be obtained from, for example, a soap bar or a liquid body wash.

An important component of these water soluble sheets is a so-called "base composition," which includes a water soluble film forming polymer, a polyvinyl alcohol, and a humectant such as propylene glycol. Surfactant may be added to the liquid base composition so that, when the composition is dried into sheet form, the sheet will generate foam when exposed to water and have cleansing properties. At this stage, skin care ingredients may also be added to the base composition in addition to or in place of the surfactant. Moreover, volatile alcohols or hydrocarbons may also be incorporated into the liquid base composition to facilitate drying of the composition to form the flexible sheet product.

DETAILED DESCRIPTION OF THE INVENTION

The present invention relates to a water soluble sheet product formed from a novel base composition. Even without the addition of other ingredients, the base composition, if allowed to dry, will form a water soluble sheet. As used herein, all weights given represent the weight of the material in a 100% active form in the composition.

The base composition includes from about 0.75% to about 5% by weight of a water soluble polymer, from about 6.5% to about 23% by weight of polyvinyl alcohol, and from about 0.75% to about 12% be weight of a humectant, with the preferred humectant being propylene glycol. The remainder of the base composition is water. Up to about 2% by weight of magnesium aluminum silicate may also be added to the base composition to enhance its slip characteristics. However, magnesium aluminum silicate results in a more viscous base composition, which, in turn, effects the thickness of the resulting soluble sheet product.

The preferred water soluble polymer is polyvinylpyrrolidone (PVP), and the most preferred PVP is 2-pyrrolidone, 1-ethenyl-homopolymer having an average molecular weight of about 60,000 Daltons. Such PVP is available as PVP K-30 from International Speciality Products, in Wayne, N.J. Although it has been discovered that PVP is the water soluble polymer which works best in the base composition of the present invention, other water soluble polymers may be used in place of or in combination with PVP. These water soluble polymers include polyquaternium 10, magnesium aluminum silicate, VP/VA copolymer, ethyl ester of PVM/MA copolymer, and sodium magnesium silicate. A suitable polyquaternium 10 is available as Celquat CS 230M from National Starch in Bridgewater, N.J. A suitable VP/VA copolymer is available as PVA 735 from International Specialty Products in Wayne, N.J. A suitable ethyl ester of PVM/MA is available as Omnirez 2000 from International Specialty Products in Wayne, N.J. An acceptable sodium magnesium silicate is available as Veegum K from R. T. Vanderbilt in Norwalk, Conn. The level of water soluble polymer or combination of water soluble polymers used in the base composition should range from about 0.75% to about 5% by weight.

In the present invention, the polyvinyl alcohol functions as a film former, and it is used in conjunction with the water soluble polymer. In the preferred embodiment of the invention, the polyvinyl alcohol used has a hydrolysis of between about 87% and 90%. A suitable polyvinyl alcohol having the preferred hydrolysis range is available as AirVol polyvinyl alcohol supplied by Air Products and Chemicals, Inc. in Allentown, Pa. Either AirVol 540, having a hydrolysis of between about 87% and 89%, or AirVol 523S, having a hydrolysis of between about 87% and 90% is preferred. In the most preferred embodiment of the invention, AirVol 523S is used because it best enhances the solubility of the soluble sheet product. It has been found that a polyvinyl alcohol having a hydrolysis below 87% results in a sheet which is less soluble. Above 90%, the sheet again loses some solubility.

The preferred humectant is propylene glycol, which serves to aid the sheet product to absorb water. In addition to propylene glycol, other humectants which can be used as the humectant in the base composition of the present invention include: (1) glycerin; (2) dipropylene glycol; (3) glyceryl polymethracrylate; and (4) glyceryl polymethracrylate in combination with propylene glycol. The level of humectant used in the base composition is normally from about 0.75% to about 12% by weight. However, additional humectant can be added depending upon the end use and desired characteristics of the soluble sheet. However, the amount of humectant added should not adversely effect the formation of the soluble sheet product.

In the preferred embodiment of the base composition, from about 1.5% to about 2.5% by weight of PVP, from about 13.5% to about 14.5% by weight of polyvinyl alcohol, and from about 2.5% to about 3.5% of propylene glycol are used. In the most preferred embodiment, about 1.75% of a PVP having an average molecular weight of about 60,000 Daltons, about 13.91% of polyvinyl alcohol having a hydrolysis between about 89% and 90%, and about 2.94% of propylene glycol are used. The balance of the base composition is water.

In preparing the base composition of this invention, the water soluble polymer and water are placed into a heatable container. With constant agitation, polyvinyl alcohol is then slowly added to the water and water soluble polymer mixture. When the polyvinyl alcohol has become saturated (starts to swell), heat is applied until the mixture reaches about 180° F. The mixture is agitated throughout the heating process. Once the mixture has reached 180° F., heating is discontinued. At this point, the humectant is added. Preferably, agitation is continued until the mixture has cooled to about 120° F., although additives and water my be added to the base composition while it is still hot. The base composition can be stored in a tightly covered container. If it is to be stored for a long period of time prior to its use for formation of the sheet product, a preservative such as DMDM hydantion may be added. A suitable DMDM hydantion is available as Mackstat DM from McIntyre in University Park, Ill.

In accordance with the present invention, various ingredients may be combined with the base composition depending upon the intended use of the final product. As used herein, the combination of base composition and surfactant and/or other ingredients is referred to as the liquid product composition. I have found that the base composition is compatible with a rather wide variety of surfactants, emollients, humectants, beads, exfoliating agents, colorants and fragrance additives. Once the desired ingredients have been combined with such the base composition, the resulting liquid product composition is then dried to form the water soluble sheet product. When the base composition is combined with such other ingredients, the level of PVP, polyvinyl alcohol, and propylene glycol in the liquid product composition should be as follows: about 0.15% to about 0.35% by weight of PVP; about 1.3% to about 2.78% by weight of polyvinyl alcohol; and about 0.15% to about 0.59% by weight of propylene glycol. In general, a liquid product composition useful for skin conditioning can include up to about 50% by weight of skin feel ingredients, about 15% to about 90% by weight of the base composition, with the balance of the liquid product composition being water. Although up to about 50% by weight of the liquid product composition may be skin feel ingredients, depending upon the chosen skin feel ingredient, less than 50% by weight of the liquid product composition should be used if formation of the soluble sheet product is adversely effected.

In general, when surfactant is added to the base composition, a composition useful for personal cleansing should include about 15% to about 90% by weight of the base composition, and to up to about 65% by weight of surfactant. As is discussed in more detail below, water soluble soaps, anionic surfactants, nonionic surfactants, cationic surfactants, and surfactant blends may all be added to the base composition. The combined weight of surfactant should not exceed about 65% by weight of the liquid product composition; however, the amount of surfactant which can be added without adversely effecting the formation of the soluble sheet product depends upon the chosen surfactant.

When the base composition is blended with selected ingredients, it is preferred that the combination of the base composition and such ingredients include about 20% by weight of base composition. However, the amount of base composition used will vary depending upon the desired viscosity of the liquid product composition and the corresponding desired thickness of the soluble sheet product. In general, the more viscous the liquid product composition is, the thicker the soluble sheet product formed from the liquid product composition will be. The amount of surfactant added will vary depending upon the particular surfactant chosen and the effect desired by the user. The addition of water is not required for blending the base composition with a surfactant, but the change in the viscosity of the base composition and surfactant mixture caused by the addition of water will assist in the dispersal of additive components. Dilution with water will also reduce product cost and produce thinner sheets.

In connection with the disclosure of surfactants, soaps, skin feel ingredients and other ingredients, various exemplary formulations are given. These examples are illustrative only, and they are not intended and do not limit the invention in any way.

Anionic surfactants are the preferred surfactants for use with the base composition of the present invention. Anionic surfactants which are compatible with the base composition include ammonium laureth sulfate, sodium laureth sulfate, and TEA-cocoyl glutamate. A suitable ammonium laureth sulfate is available as Standapol A from Cognis in Ambler, Pa. Sodium laureth sulfate is also available from Cognis as Standapol ES-2. A suitable TEA-cocoyl glutamate is available as Amisoft CT-125 from Ajinomoto USA, Inc. in Teaneck, N.J.

When used as the surfactant in the making of the flexible sheet product of the present invention, anionic surfactants produce a quick and long lasting lather. Up to about 47% by weight of anionic surfactant can be added to the base composition of the present invention. The following are representative formulations embodying the present invention where anionic surfactants are mixed with the base composition to form a liquid product composition which may then be dried to form the soluble sheet product. As used in the Examples 1 through 5 below, the base composition includes about 1.75% PVP K-30, about 13.91% AirVol 523S, about 2.94% propylene glycol, and about 81.4% water.

EXAMPLE 1

| Ingredient | Percentage by Weight |
| --- | --- |
| Base Composition | 20–21% |
| Ammonium Laureth Sulfate | 20%–24% |
| Deionized Water | Balance |

EXAMPLE 2

| Ingredient | Percentage by Weight |
| --- | --- |
| Base Composition | 20–21% |
| Ammonium Laureth Sulfate | 10–12% |
| Deionized Water | Balance |

EXAMPLE 3

| Ingredient | Percentage by Weight |
| --- | --- |
| Base Composition | 89–90% |
| Sodium Laureth Sulfate | 2.5–3% |
| Deionized Water | Balance |

EXAMPLE 4

| Ingredient | Percentage by Weight |
| --- | --- |
| Base Composition | 20–21% |
| Sodium Laureth Sulfate | 14–18% |
| Deionized Water | Balance |

EXAMPLE 5

| Ingredient | Percentage by Weight |
| --- | --- |
| Base Composition | 20–21% |
| TEA-Cocoyl Glutamate | 17–18% |
| Deionized Water | Balance |

Nonionic surfactants may also be added to the base composition of the present invention. However, when used as the only surfactant, such a mixture of nonionic surfactants with the base composition will not form sheets. Consequently, in order to achieve the formation of the desired soluble sheet product, it is necessary to include a companion surfactant, such as an anionic surfactant, cationic surfactant, amphoteric surfactant, or a surfactant blend. Depending to a degree upon the nonionic surfactant chosen, up to about between 26% and 30% by weight of a nonionic surfactant can be incorporated into the liquid product composition. In general, nonionic surfactant may be added to the base composition until the point at which film formation, and, consequently, the formation of the soluble sheet product, is adversely effected. However, in order to achieve sheet formation, the total amount of nonionic and other surfactant added should not exceed about 65% by weight of the liquid product composition. In order to form satisfactory sheets, the nonionic surfactant should be added to the base composition in lower levels than the other surfactants to be included in the mixture.

Cationic surfactants can also be used to form the sheets of the present invention. Compatible cationic surfactants include DL pyrrolidone carboxylic acid ethyl cocoyl arginate and sunflowerseedamidopropyl dimethylamine lactate. A suitable DL pyrrolidone carboxylic acid ethyl cocoyl arginate is available as CAE from Ajinomoto USA, Inc. in Teaneck, N.J. Depending upon the cationic surfactant selected, up to about between 4.9% and 48% by weight of cationic surfactant can be incorporated into the liquid product composition. The maximum level of surfactant will vary depending upon the particular cationic surfactant chosen. Thus, in order to obtain formation of the soluble sheet product, it has been discovered that the maximum level of DL pyrrolidone carboxylic acid ethyl cocoyl arginate that can be added to the liquid composition is about 4.9% by weight, and the maximum level of sunflowerseedamidopropyl dimethylamine lactate that can be incorporated into the liquid product composition is about 12% by weight. In general, cationic surfactant may be added to the base composition until the point at which film formation, and consequently, the formation of the sheet, is adversely effected.

When DL pyrrolidone carboxylic acid ethyl cocoyl arginate (CAE) is added to the base composition and dried to form the flexible sheet product, a stretchy, thin sheet which quickly dissolves in water is formed. In order to prevent over-dryness of the sheet, the DL pyrrolidone carboxylic acid ethyl cocoyl arginate should be solublized in propylene glycol prior to addition to the base composition. Following is a representative formulation embodying the present invention of the combination of a base composition and surfactant mixture using DL pyrrolidone carboxylic acid ethyl cocoyl arginate. As used in Example 6 and 7, the base composition includes about 1.75% PVP K-30, about 13.91% AirVol 523S, about 2.94% propylene glycol, and about 81.4% water.

EXAMPLE 6

| Ingredient | Percentage by Weight |
| --- | --- |
| Base Composition | 20–21% |
| CAE | 4–4.9% |
| Propylene Glycol | 44–45% |
| Deionized Water | Balance |

In mixtures containing DL pyrrolidone carboxylic acid ethyl cocoyl arginate, foam production of the sheet may be enhanced by the addition of a betaine. Nevertheless, it has been found that limited foam is generated by a mixture containing DL pyrrolidone carboxylic acid ethyl cocoyl arginate unless an anionic surfactant is also added to the mixture. The following is an example of a preferred mixture including DL pyrrolidone carboxylic acid ethyl cocoyl arginate and an anionic surfactant, sodium laureth sulfate:

EXAMPLE 7

| Ingredient | Percentage by Weight |
| --- | --- |
| Base Composition | 19–20% |
| CAE | 2–3% |
| Sodium Laureth Sulfate | 7–9% |
| Propylene Glycol | 28.5%–29.5% |
| Deionized Water | Balance |

As previously noted, in order to achieve the formation of suitable sheets, the total amount of cationic and other surfactant added should not exceed about 65% by weight of the liquid product composition.

Water soluble soaps can also be used in the formation of the soluble sheet product of the present invention. It can be used to modify the lather generation potential of the soluble sheet and to slow the solubility of the sheet. Up to about between 2% and 22% weight of soap can be incorporated into the liquid product composition, depending upon the soap chosen. In general, soap and synthetic surfactant may be added to the base composition until the point at which film formation, and consequently, the formation of the soluble sheet product, is adversely effected. Soap can be the only surfactant added to the base composition, or, alternatively, it may be combined with another surfactant for addition to the base composition. In order to achieve the formation of sheets, the total amount of soap and synthetic surfactant should not exceed about 65% by weight of the liquid product composition. Compatible soaps include sodium octonoate and potassium soaps. The following is an example of a composition using sodium octonoate. As used in Example 8, the base composition includes about 1.75% PVP K-30, about 13.91% AirVol 523S, about 2.94% propylene glycol, and about 81.4% water.

EXAMPLE 8

| Ingredient | Percentage by Weight |
| --- | --- |
| Base Composition | 19.5–20.5% |
| Sodium Octonoate | 9–10% |
| Sodium Laureth Sulfate | 12–15% |
| Deionized Water | Balance |

Triethanolamine potassium vegetable oil soap is also a compatible soap and is available as Mackanate WGS from McIntyre in University Park, Ill. The following is an example of a mixture with Mackanate WGS. As used in Example 9, the base composition includes about 1.75% PVP K-30, about 13.91% AirVol 523S, about 2.94% propylene glycol, and about 81.4% water.

EXAMPLE 9

| Ingredient | Percentage by Weight |
| --- | --- |
| Base Composition | 19.5–20.5% |
| Mackanate WGS | 19.5–20.5% |
| Deionized Water | Balance |

Skin feel ingredients, including skin conditioners such as vitamin E acetate, silicones, petrolatum and aloe may be added to the base composition with or without a surfactant. When used without a surfactant, a sheet containing such skin conditioning additives may be applied directly to wet skin, such as right after bathing or showering. When the sheet with skin conditioning additives is applied to wet skin, the sheet dissolves leaving the skin conditioner on the skin.

Other skin feel ingredients may also be added to the liquid product composition to provide visual or perceptual sensory or skin conditioning effects to the ultimate product. Examples include loofah, jojoba beads, oat hulls, walnut shells, petrolatum, cyclomethicone, sodium PEG-7 olive oil carboxylate, silicones, aloe, vitamin E acetate, emollients and humectants. These skin feel ingredients can be added at levels required for aesthetic sensory perception, or skin conditioning and have the ability to change the texture of the sheet itself.

Skin feel ingredients added to the liquid product composition at provide visual perceptual sensory, or skin conditioning effects, may be added at the level desired by the user; however, the amount of material added should not impair film formation to create the soluble sheet product. In general, a liquid product composition. Although up to about 50% by weight of the liquid product composition may be skin feel ingredients, depending upon the chosen skin feel ingredient, less than 50% by weight of the liquid product composition may have to be used in order to avoid adversely effecting the formation of the soluble sheet product.

The following examples further illustrate the present invention in which skin feel ingredients which enhance the visual or perceptual sensory or skin conditioning effects are added. These examples are not intended to limit the invention in any way. Thus, altering the examples, or even using altogether different ingredients which are within the scope of the claims is not outside the contemplated invention. As used in Examples 10 through 14, the base composition includes about 1.75% PVP K-30, about 13.91% AirVol 523S, about 2.94% propylene glycol, and about 81.4% water.

EXAMPLE 10

| Ingredient | Percentage by Weight |
| --- | --- |
| Base Composition | 19–20% |
| TEA–Cocoyl Glutamate | 18–19% |
| Sodium PEG–7 Olive Oil Carboxylate | 7–8% |
| Deionized Water | Balance |

EXAMPLE 11

| Ingredient | Percentage by Weight |
| --- | --- |
| Base Composition | 21–22% |
| Sodium Laureth Sulfate | 9–12% |
| Sodium PEG-7 Olive Oil Carboxylate | 11–12% |
| Deionized Water | 28–29% |

EXAMPLE 12

| Ingredient | Percentage by Weight |
| --- | --- |
| Base Composition | 22–23% |
| Ammonium Laureth Sulfate | 10–13% |
| High Oleic Sunflower Seed Oil | 11–12% |
| Perfume, Dye, etc. | 1.5–2.5% |
| Deionized Water | Balance |

EXAMPLE 13

| Ingredient | Percentage by Weight |
| --- | --- |
| Base Composition | 23.5–24.5% |
| Ammonium Laureth Sulfate | 9–12% |
| Cetearyl Octonoate | 10–11% |
| Perfume, Dye, etc. | 5–6% |
| Deionized Water | Balance |

EXAMPLE 14

| Ingredient | Percentage by Weight |
| --- | --- |
| Base composition | 42.5–43.5% |
| Ammonium Laureth Sulfate | 13–17% |
| Jojoba Ester | 2–3% |

Antibacterial agents such as triclosan, benzethonium chloride, chlorohexidine gluconate (CHG) and triclocarban may also be incorporated into the liquid product composition.

In the above examples surfactants are used which are typically used in a variety of personal care cleansing products. However, surfactants which are usually employed in household cleaning products such as laundry detergents may also be used in the soluble sheet product. Such an embodiment has particular application to treatment of stains on clothing. In this embodiment of the invention, sheets formed by including such surfactants in the base composition are dampened and applied to the stained area. The sheet is then allowed to remain on the stained area, providing treatment to the stain, until washing occurs.

Volatile ingredients such as ethanol, petroleum ether, or isopentane can be incorporated into the liquid product composition to help enhance the drying of the soluble sheet product. These volatile materials serve to expand the liquid product, and, at room temperature, cause a skin to form over the inflated surface of the product. In the dried soluble sheet product, the skin remains semi-inflated, creating air pockets, or cells, in the soluble sheet product. Air pockets may also be created in the soluble sheet product by aerosolizing the liquid product composition. Alternatively, air pockets may be created in the soluble sheet product by incorporating surfactant and certain oils into the liquid product composition. For example, an addition of about 11% of sunflower oil to the base composition and about 10–12% ammonium laureth sulfate results in a soluble sheet product with air pockets or cells.

Once the desired ingredients have been incorporated into the base composition, the liquid product composition is preferably is spread onto a relatively flat surface to dry at room temperature. Alternatively, the liquid may be more rapidly dried by subjecting it to a heat, such as an oven. It has been found that drying the liquid product composition in about a 140° F. oven works well. However, higher temperature can be used for faster drying. Enhanced drying can also be accomplished through a heated spray system, vacuum, or other known drying methods.

What is claimed is:

1. A water soluble sheet formed from a composition comprising a water soluble polymer, polyvinyl alcohol, a humectant, and skin feel ingredients.

2. A base composition for use in preparing a water soluble sheet product, said base composition comprising water and about 0.75% to about 5% by weight of a water soluble polymer, said water soluble polymer comprising PVP, said PVP further comprising 2-pyrrolidone, 1-ethenyl-homopolymer, about 6.5% to about 23% by weight of polyvinyl alcohol, and about 0.75% to about 12% by weight of a humectant.

3. The base composition of claim 2 wherein said polyvinyl alcohol has a hydrolysis of between about 87% and 90%.

4. The base composition of claim 2 wherein said humectant is propylene glycol.

5. A composition for use in preparing a water soluble sheet product, said composition comprising up to about 65% by weight of a surfactant, about 0.15% to about 0.35% by weight of a water soluble polymer, said water soluble polymer comprising PVP, said PVP further comprising 2-pyrrolidone, 1-ethenyl-homopolymer, about 1.3% to about 2.78% by weight of polyvinyl alcohol, about 0.15% to about 0.59% by weight of a humectant, with the balance of the composition being water.

6. The composition of claim 5 wherein said polyvinyl alcohol has a hydrolysis of between about 87% and 90%.

7. The composition of claim 5 wherein said humectant is propylene glycol.

8. The composition of claim 5 wherein said surfactant is soap.

9. The composition of claim 5 wherein said surfactant is a surfactant blend.

10. The composition of claim 5 further including up to about 50% by weight of skin feel ingredients.

11. A composition for use in preparing a water soluble sheet product, said composition comprising up to about 50% by weight of skin feel ingredients, about 0.15% to about 0.35% by weight of a water soluble polymer, about 1.3% to about 2.78% by weight of polyvinyl alcohol, and about 0.15% to about 0.59% by weight of a humectant, with the balance of the composition being water.

12. The composition of claim 11 wherein said water soluble polymer is PVP.

13. The composition of claim 12 wherein said PVP is 2-pyrrolidone, 1-ethenyl-homopolymer.

14. The composition of claim 11 wherein said polyvinyl alcohol has a hydrolysis of between about 87% and 90%.

15. The composition of claim 11 wherein said humectant is propylene glycol.

16. A method for forming a water soluble sheet product, said method comprising:
   a. Forming a base composition comprising about 0.75% to about 5% by weight of a water soluble polymer, said water soluble polymer comprising PVP, said PVP further comprising 2-pyrrolidone, 1-ethenyl-homopolymer, about 6.5% to about 23% by weight of polyvinyl alcohol, from about 0.75% to about 12% by weight of a humectant, and water;
   b. Adding a surfactant to said base composition to form a liquid product composition, said liquid product composition being up to about 65% by weight of said surfactant, between about 15% to about 90% of said base composition, with the balance of said liquid product composition being water;
   c. Spreading said liquid product composition into sheet form; and
   d. Drying said liquid product composition.

17. The method of claim 16 wherein said polyvinyl alcohol has a hydrolysis between about 87% and 90%.

18. The method of claim 16 wherein said humectant is propylene glycol.

19. The method of claim 16 wherein said surfactant is soap.

20. The method of claim 16 wherein said surfactant is a surfactant blend.

21. The method of claim 16 further comprising adding up to about 50% by weight of skin feel ingredients to said surfactant and said base composition to form said liquid product composition.

22. A method for forming a water soluble sheet product, said method comprising:
   a. Forming a base composition comprising about 0.75% to about 5% by weight of a water soluble polymer, about 6.5% to about 23% by weight of polyvinyl alcohol, from about 0.75% to about 12% of a humectant, and water;
   b. Adding skin feel ingredients to the base composition to form a liquid product composition, said liquid product composition being up to about 50% of said skin feel ingredients, between about 15% to about 90% of said base composition, with the balance of said liquid product composition being water;
   c. Spreading said liquid product composition into sheet form; and
   d. Drying said product composition.

23. The method of claim 22 wherein said water soluble polymer is PVP.

24. The method of claim 23 wherein said PVP is 2-pyrrolidone, 1-ethenyl-homopolymer.

25. The method of claim 22 wherein said polyvinyl alcohol has a hydrolysis of between 87% and 90%.

26. The method of claim 22 wherein said humectant is propylene glycol.

* * * * *